United States Patent
Lee

(10) Patent No.: US 11,389,109 B2
(45) Date of Patent: Jul. 19, 2022

(54) SYSTEM AND METHOD FOR MONITORING AND TREATING HEAD, SPINE AND BODY HEALTH AND WELLNESS

(71) Applicant: Y. Michael Lee, Victor, NY (US)

(72) Inventor: Y. Michael Lee, Victor, NY (US)

(*) Notice: Subject to any disclaimer, the term of this patent is extended or adjusted under 35 U.S.C. 154(b) by 185 days.

(21) Appl. No.: 16/384,501

(22) Filed: Apr. 15, 2019

(65) Prior Publication Data

US 2019/0313967 A1    Oct. 17, 2019

Related U.S. Application Data

(60) Provisional application No. 62/657,749, filed on Apr. 14, 2018.

(51) Int. Cl.
*A61B 5/00* (2006.01)
*A61B 5/0205* (2006.01)
(Continued)

(52) U.S. Cl.
CPC .......... *A61B 5/4836* (2013.01); *A61B 5/0024* (2013.01); *A61B 5/0205* (2013.01);
(Continued)

(58) Field of Classification Search
CPC ....... A61B 5/0024; A61B 5/0077; A61B 5/02; A61B 5/0205; A61B 5/02416;
(Continued)

(56) References Cited

U.S. PATENT DOCUMENTS

| 4,055,168 A | 10/1977 | Miller et al. |
| 5,158,089 A | 10/1992 | Swezey et al. |

(Continued)

FOREIGN PATENT DOCUMENTS

| JP | 2009018158 | 1/2009 |
| WO | 2005067796 | 7/2005 |

OTHER PUBLICATIONS

Chang, K.M., Chen, S.H., Lee, H.Y., Ching, C.T.S. and Huang, C.L., 2012. A wireless accelerometer-based body posture stability detection system and its application for meditation practitioners. Sensors, 12(12), pp. 17620-17632.
(Continued)

*Primary Examiner* — Carl H Layno
*Assistant Examiner* — Jane C Kalinock
(74) *Attorney, Agent, or Firm* — IPro, PLLC

(57) ABSTRACT

Real-time head and spine alignment, position and other physiological parameters are detected to measure human being health and wellness status. A wearer is reminded to actively correct spinal curvatures and the system may further interfere if head and spinal mal-position or other injury or disease parameters are detected by the system's sensor devices. The system includes wearable universal sensor modules that are attached and detached easily from receiver units having different formats for different body locations depending on their physiological functions. The system is designed to analyze, by artificial intelligence, data from each universal sensor module and provide accurate feedback that can be used by health professionals to monitor remote individual health status and notify a wearer to prevent and correct mal-position or injury or disease status.

34 Claims, 9 Drawing Sheets

(51) Int. Cl.

| | |
|---|---|
| *A61F 5/02* | (2006.01) |
| *A61B 7/00* | (2006.01) |
| *A61B 5/1455* | (2006.01) |
| *A61B 5/024* | (2006.01) |
| *A61B 5/11* | (2006.01) |
| *A61B 3/11* | (2006.01) |
| *A61B 3/113* | (2006.01) |
| *A61B 5/16* | (2006.01) |
| *A61B 3/14* | (2006.01) |
| *A61B 5/12* | (2006.01) |
| *A61B 7/04* | (2006.01) |
| *A61B 5/389* | (2021.01) |

(52) U.S. Cl.
CPC ............ *A61B 5/486* (2013.01); *A61B 5/6824* (2013.01); *A61B 5/6898* (2013.01); *A61B 5/742* (2013.01); *A61B 5/7455* (2013.01); *A61F 5/02* (2013.01); *A61B 3/112* (2013.01); *A61B 3/113* (2013.01); *A61B 3/14* (2013.01); *A61B 5/0077* (2013.01); *A61B 5/02416* (2013.01); *A61B 5/1107* (2013.01); *A61B 5/1124* (2013.01); *A61B 5/123* (2013.01); *A61B 5/14551* (2013.01); *A61B 5/16* (2013.01); *A61B 5/389* (2021.01); *A61B 5/4561* (2013.01); *A61B 5/4803* (2013.01); *A61B 7/006* (2013.01); *A61B 7/04* (2013.01); *A61B 2562/0219* (2013.01)

(58) Field of Classification Search
CPC ... A61B 5/0488; A61B 5/1077; A61B 5/1107; A61B 5/1116; A61B 5/1124; A61B 5/123; A61B 5/16; A61B 5/4561; A61B 5/4803; A61B 5/4836; A61B 5/486; A61B 5/6816; A61B 5/6824; A61B 5/6831; A61B 5/6898; A61B 5/742; A61B 5/7455; A61B 5/14551; A61B 7/006; A61B 7/04; A61B 2562/0219; A61B 3/112; A61B 3/113; A61B 3/14; A61B 2562/166; A61B 2562/226
USPC .......................................................... 600/301
See application file for complete search history.

(56) References Cited

U.S. PATENT DOCUMENTS

| | | | |
|---|---|---|---|
| 5,469,861 A | 11/1995 | Piscopo et al. | |
| 6,047,203 A | 4/2000 | Sackner et al. | |
| 6,514,218 B2 | 2/2003 | Yamamoto | |
| 6,551,252 B2 | 4/2003 | Sackner et al. | |
| 7,471,290 B2 | 12/2008 | Wang et al. | |
| 7,664,546 B2 | 2/2010 | Hartley et al. | |
| 8,157,752 B2 | 4/2012 | Fischer | |
| 8,818,748 B2 | 8/2014 | Hatlestad et al. | |
| 8,928,484 B2 | 1/2015 | Chang et al. | |
| 9,406,211 B2 | 8/2016 | Sahiholnasab et al. | |
| 9,504,410 B2 | 11/2016 | Yoav | |
| 9,750,429 B1 | 9/2017 | Sackner et al. | |
| 9,839,553 B2 | 12/2017 | Bannister et al. | |
| 9,913,613 B2 | 3/2018 | Gal | |
| 10,206,639 B2 | 2/2019 | Verma et al. | |
| 2004/0027246 A1 | 2/2004 | Aguglia | |
| 2007/0078324 A1 | 4/2007 | Wijisiriwardana | |
| 2008/0082018 A1 | 4/2008 | Sackner et al. | |
| 2010/0037489 A1* | 2/2010 | Berner, Jr. | A43B 13/00 36/136 |
| 2010/0185076 A1 | 7/2010 | Jeong et al. | |
| 2013/0207889 A1* | 8/2013 | Chang | G01P 15/00 345/156 |
| 2013/0243285 A1 | 9/2013 | Wang et al. | |
| 2014/0122958 A1* | 5/2014 | Greenebrg | A61B 5/112 714/748 |
| 2014/0142485 A1* | 5/2014 | Berry | A61B 5/1116 602/19 |
| 2015/0366504 A1* | 12/2015 | Connor | A61B 5/0492 600/301 |
| 2016/0066834 A1* | 3/2016 | Baldwin | A61B 5/0051 600/552 |
| 2016/0157779 A1* | 6/2016 | Baxi | A61B 5/6831 600/301 |
| 2016/0183836 A1* | 6/2016 | Muuranto | A61B 5/0022 600/301 |
| 2016/0220174 A1 | 8/2016 | Yip et al. | |
| 2016/0249174 A1 | 8/2016 | Patel et al. | |
| 2016/0310065 A1 | 10/2016 | Arif | |
| 2016/0310071 A1* | 10/2016 | Kim | A61B 5/6898 |

OTHER PUBLICATIONS

Ding, Z.Q., Luo, Z.Q., Causo, A., Chen, I.M., Yue, K.X., Yeo, S.H. and Ling, K.V., 2013. Inertia sensor-based guidance system for upperlimb posture correction. Medical engineering & physics, 35(2), pp. 269-276.

Cho, G., Jeong, K., Paik, M.J., Kwun, Y. and Sung, M., 2011. Performance evaluation of textile-based electrodes and motion sensors for smart clothing. IEEE Sensors Journal, 11(12), pp. 3183-3193.

Lumo Lift: The First Wearable Posture Coach. You slouch, it vibrates! A posture corrector that's perfect for sitting or working at computers. Comfortable & easy to use. Improve your posture today!(https://www.amazon.com/Lumo-Lift-corrector-computers-Comfortable/dp/B00N9P8GM—accessed Dec. 28, 2018).

Isabel Pfab: A Wearable Intervention for Posture Improvement, MSc. Thesis, 2016, January. See pp. 116-117 of PDF for sketches of devices.

* cited by examiner

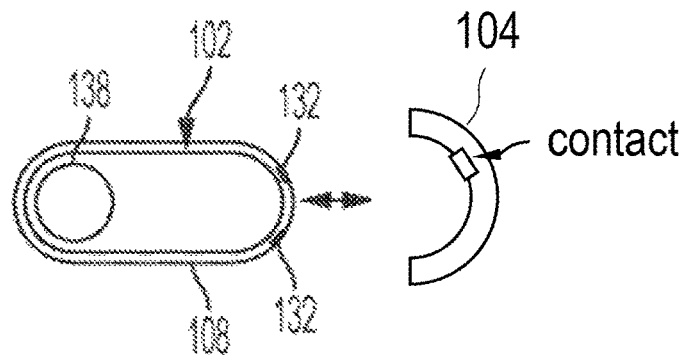
Location 1
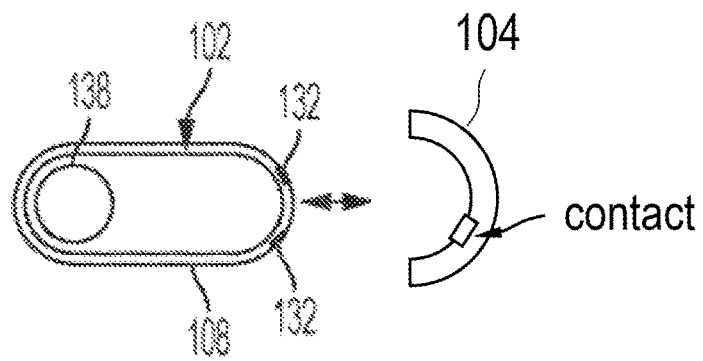
Location 2
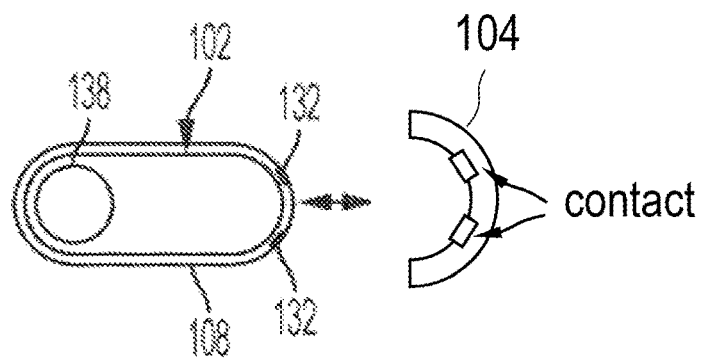
Location 3
FIG. 11

SYSTEM AND METHOD FOR MONITORING AND TREATING HEAD, SPINE AND BODY HEALTH AND WELLNESS

CROSS-REFERENCE TO RELATED APPLICATIONS

This application claims the benefit of U.S. Provisional Patent Application No. 62/657,749, filed Apr. 14, 2018, entitled WEARABLE DEVICE FOR HEAD AND SPINE MONITORING, the entirety of which is incorporated herein by reference.

FIELD OF THE INVENTION

The present invention relates to system, method and apparatus that measures human being health and wellness status: head and spine alignment monitoring and correcting device, including head, cervical-thoracic-lumbar spine, joints and other musculoskeletal, neurological status, cardiopulmonary parameters; in particular, to a system and method utilizing wearable universal multimodality sensor modules that can be located at different positions of the head, spine and/or limbs; and more particularly to a system and method utilizing wearable universal multimodality sensor modules that can not only detect the head, cervical, thoracic lumbar spine and other musculoskeletal alignment indexes and neurological functional status, but also other physiological parameters, such as pulmonary and cardiovascular characters. This application discloses a novel way to detect real time head, spine and other body physiological parameters, and analyze by artificial intelligence the data from these modules and provide accurate feedback that can be used for health professional to monitor remote individual health status, assist the user to actively correct malalignment and notify user to prevent and treat mal-position or injury or disease status.

BACKGROUND OF THE INVENTION

Spine and related musculoskeletal plus neurological pain are the highest cost chronic condition. Eighty percent (80%) of Americans experience back pain at some point in their lives, with thirty percent (30%) of U.S. adults suffering from low back pain within last 3 months. Except for a cold, back pain is the second most abundant reason for missed work days and clinician visits with total direct healthcare cost exceeding $90 billion dollars a year.

Several reasons have been identified as sources of back pain, neck pain and spine misalignment, including the increasingly excessive usage of electronic devices and sports injuries. With the increase use of electronic devices, including cell phones, games and computers, many spinal misalignments occur now among a younger population, instead of in people following certain injuries or the elderly population. Excessive use of portable electronic devices can significantly increase neck and back pain because of the biomechanical force and alignment change of the cervical, thoracic and lumbar spine. A smaller range of motion between flexion and extension has also been correlated with pain and mechanical instability. Medical professionals advise that neck and back pain be reduced by maintaining a neutral position, along with appropriate exercise.

According to the recent SRS-Schwab classification which provides the mechanism to assess cervical and thoracic lumbar deformity within the framework of global spinopelvic misalignment and clinically relevant parameters, surgical or preventive alignment correction can be made in order to minimize focal kyphosis, scoliosis and spondylolisthesis. However, there is yet any scientific evidence to support the specific alignment corresponds to a specific deformity.

Current systems detect poor body posture with an electronic device that transmits a signal to a portable device that can display limited information of the body posture and notify the user of poor posture. However, these systems do not provide detailed cervical, thoracic and lumbar spine curvature and alignment index measurement and possible correction.

Therefore, there is a need for a system and method that detects and transmits detailed head, neck, and spine alignment data, as well as neurological and musculoskeletal data from other parts of the body which may be indicative of head, spine and body alignment and neurological function. The present invention addresses these as well as other needs.

BRIEF SUMMARY OF THE INVENTION

In accordance with an aspect of the present invention, a system and method for monitoring and treating head, spine and body abnormalities may include a plurality of universal modules that can be fit in at different positions of the head, spine and other body part. Each module may contain multimodality sensors that can not only detect the head, cervical, thoracic, lumbar and other musculoskeletal alignment indexes, but also the body's neurological status and other physiological parameters, such as pulmonary and/or cardiovascular characters. In a further aspect, the universal capsule modules can be fit into different, specially designed carriers which are configured for different body parts whereby activation of selective sensors can differentiate physiological detection and notification functions for each body location. The system and method may also remind and assist a wearer to actively correct curvatures and may provide further interference if head and spinal mal-position or other injury or disease parameters are detected by the sensor devices.

In accordance with another aspect of the present invention, the system and method to detect head, spine and body alignment change may be combined and matched with external body photographic images focusing on a dynamic analysis of the head, cervical, thoracic and lumbar spine, pelvis and other body parts so as to define the detailed professional dynamic head, spine and body alignment parameters including cervical lordosis angle, cervical SVA, pelvic incidence, lumbar lordosis angle, pelvic tile, SVA et al. Such body photographic measurements may be equivocal to those provided by professional medical image. Medical images such as x-ray, CT and MRI, may be used to match body photographic image performed by machine learning to calibrate the initial spine or body position for each sensor module and to calculate the normal range of motion for each individual irrespective of body shape, height, or even what kind of clothes they are wearing. To that end, the system and method of the present invention includes software algorithms to calculate the angle, distance and curvature with consideration to the spine and other body parts. As a result, the system and method are designed to analyze the data from the sensor modules and provide accurate feedback that can be used by health professionals to monitor remote individual health status and notify users to prevent and correct mal-position or injury or disease status.

It is, therefore, an aspect of the present invention to provide a method for monitoring and treating head, spine and body abnormalities comprising, as shown in FIG. 9, a) providing a plurality of receiver units wherein each receiver unit is configured to be secured at a selected location on a wearer's body; b) mounting a universal multimodality sensor module comprising a power source, a printed circuit board including a processor, memory and communication module, and a plurality of individual sensors to each respective receiver unit, wherein one or more selected individual sensors within the each respective multimodality sensor module is powered depending upon the selected location of its respective receiver unit on the wearer's body; and c) sensing at regular intervals, using the one or more powered selected individual sensors, health data related to the head, spine or body movements of the wearer. In a further aspect, the method may also include d) communicating, via the communication module, the sensed data to a computing device including a computer processor and a computer memory; and e) comparing, via the computer processor, the sensed data with a prepopulated data range stored in the computer memory. And still further, f) delivering a notification to the wearer if the sensed data is outside of the prepopulated range so that the wearer may adjust one or more of their head, spine or body position until the sensed data returns to the prepopulated range.

In still another aspect of the present invention, each universal multimodality sensor module comprises a 9-axis accelerometer, a pulse oximeter, an electromyography (EMG) sensor and a mechanomyography (MMG) sensor. The one or more of the universal multimodality sensor modules may further comprises a feedback device in communication with the computing device. When the sensed data is outside of the prepopulated range, the feedback device is triggered to deliver the notification. The feedback device may comprise one or both of a haptic device configured to vibrate and a light emitting diode (LED) configured to emit a steady light or flashing light. In a further aspect, the one or more of the universal multimodality sensor modules further comprises a speaker/microphone and auditory sensor/processor, wherein the method further includes a) recording joint friction auditory information using the speaker/microphone; b) filtering the auditory information using the auditory processor; c) amplifying the filtered auditory information; and d) communicating the amplified filtered auditory information to the computing device. The speaker/microphone may be a bone conduction speaker/microphone. Additionally or alternatively, one or more of the universal multimodality sensor modules further comprises a selectively switchable speaker/microphone, wherein the speaker/microphone can be selectively activated to record patient generated data in combination with the other sensed health data.

It is still another aspect of the present invention to provide a system for monitoring and treating head, spine and body abnormalities. The system includes a plurality of receiver units wherein each receiver unit is configured to be secured at a selected location on a wearer's body and plurality of universal multimodality sensor modules, each comprising one or more individual sensors, a power source, a printed circuit board including a processor, memory and communication module, wherein a respective multimodality sensor module is coupled with a respective receiver. One or more selected individual sensors within each respective multimodality sensor module is powered depending upon the selected location of its respective receiver unit on the wearer's body. Health data related to the head, spine or body movements of the wearer is sensed at regular intervals using the one or more powered selected individual sensors. The system may also include a computing device including a computer processor and a computer memory, wherein the communication module communicates the sensed data to the computer processor whereby the computer processor compares the sensed data with a prepopulated data range stored in the computer memory. The computing device may be a mobile computing device, such as a smartphone, smartwatch or tablet computer.

In another aspect, of the system of the present invention, each universal multimodality sensor module may include a 9-axis accelerometer, a pulse oximeter, an electromyography (EMG) sensor and a mechanomyography (MMG) sensor. The one or more universal multimodality sensor modules may further comprise a feedback device in communication with the computing device. When the sensed data is outside of the prepopulated range, the feedback device is triggered to deliver the notification. The feedback device may be one or both of a haptic device configured to vibrate and a light emitting diode (LED) configured to emit a steady light or flashing light. Still further, one or more of the universal multimodality sensor modules may also include a speaker/microphone and auditory processor. Joint friction auditory information is recorded by the speaker/microphone, filtered and amplified by the auditory processor and communicated to the computing device. The speaker/microphone may be a bone conduction speaker/microphone. Additionally or alternatively, one or more of the universal multimodality sensor modules further comprises a selectively switchable speaker/microphone, wherein the speaker/microphone can be selectively activated to record patient generated data in combination with the sensed health data.

In still another aspect of the present invention, a first universal multimodality sensor module senses health data from a wearer's left arm and a second universal multimodality sensor module senses health data from a wearer's right arm. The computer processor may then compare the left arm health data to the right arm health data to analyze symmetry between the left arm and the right arm to judge the neurological and musculoskeletal status and other health data.

Additional aspects, advantages and novel features of the present invention will be set forth in part in the description which follows, and will in part become apparent to those in the practice of the invention, when considered with the attached figures.

BRIEF DESCRIPTION OF THE DRAWINGS

The accompanying drawings form a part of this specification and are to be read in conjunction therewith, wherein like reference numerals are employed to indicate like parts in the various views, and wherein:

FIG. 11 is a schematic showing that contacts within receiver units at different locations on a wearer may have different configurations.

DETAILED DESCRIPTION OF THE INVENTION

Dynamic spine, including cervical alignment is the crucial component of both traumatic and non-traumatic neck and back pain. Neurosurgeons, physiotherapists and other health workers typically measure active cervical range of motion (aCROM) to ascertain a patient's health problems in terms of impairments of cervical mobility so as to determine a prognosis and to evaluate the effects of physiotherapy treatment in clinical settings. The aCROM can be expressed as a "half-cycle" motion in 1 of the 6 primary movements (including flexion, extension, right and left rotation, right and left lateral bending) or "full cycle" of motion. Current research supports an understanding that a reduction of aCROM is usually seen as a clinical feature of patients with whiplash-associated disorders (WADs) and non-traumatic neck pain, like degenerative change, and therefore, special range of motion should be evaluated. Persons without neck pain showed a larger aCROM for all movements. It is also important to note that some patients are not capable of large movements.

Figures 7, 7A:
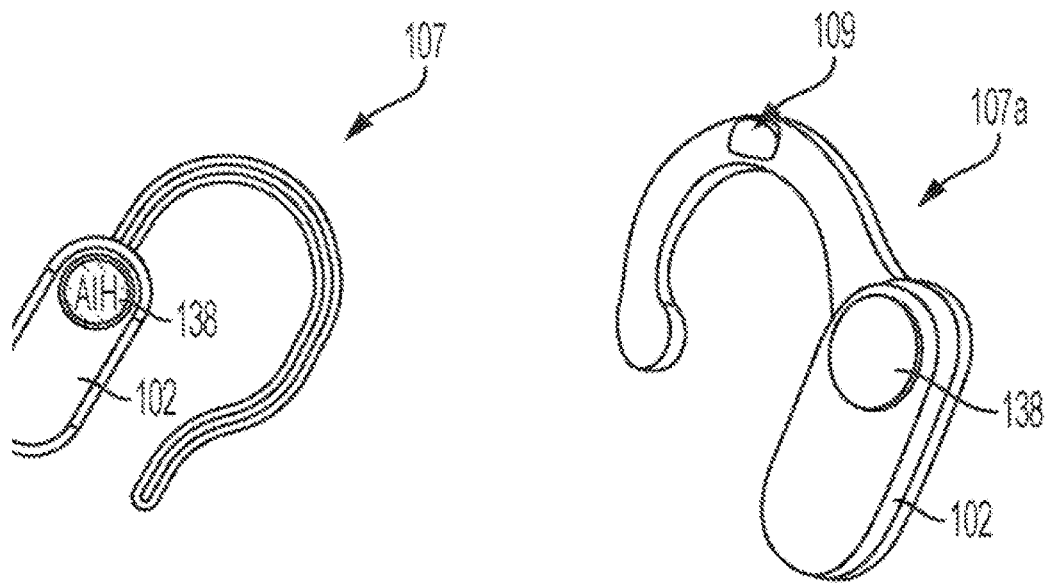
FIG. 7 is a plan view of an earpiece including a universal multimodality sensor module.
FIG. 7A is a perspective view of an alternative earpiece include a universal multimodality sensor module.
Figure 7B:
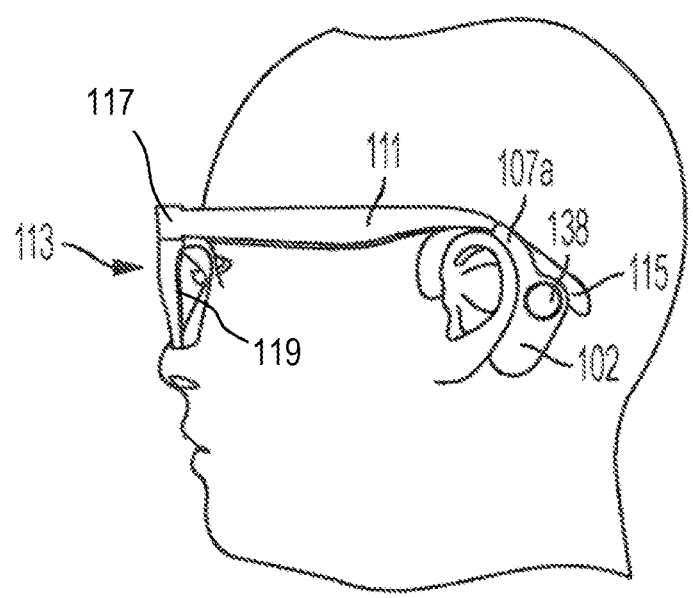
FIG. 7B is a side view of the earpiece shown in FIG. 7A being worn on a pair of glasses.

To that end, and with reference to the drawings, and FIGS. 1-5 in particular, in accordance with an aspect of the present, a system 100 for monitoring and treating head, spine and body abnormaility may include a plurality of universal multimodality sensor modules 102 secured to/within respective receiver units 104. Each receiver unit 104 is selectively positioned at a location on wearer 106, such as via an elastic band 105. (See also FIGS. 7-7B; a multimodality sensor module 102 may be mounted onto an earpiece 107/107a. Earpiece 107a may further define a channel 109 for receiving temple 111 of eyeglass/sunglasses 113 therethrough so as to position multimodality sensor module 102 about the ear and proximate temple tip 115). Each multimodality sensor module 102 includes a housing 108 containing a power source (e.g., battery) 110, printed circuit board (PCB) 112 and a plurality of individual sensors which may be mounted onto PCB 112 or within or on housing 108. For example and without limitation thereto, individual sensors may include an oximeter 114, a 9-axis accelerometer 116, an ECG sensor 118 and an EMG sensor 120. Additional auxiliary sensors 122 may include an MMG sensor, a force sensor and/or a speaker/microphone.

Figure 6:
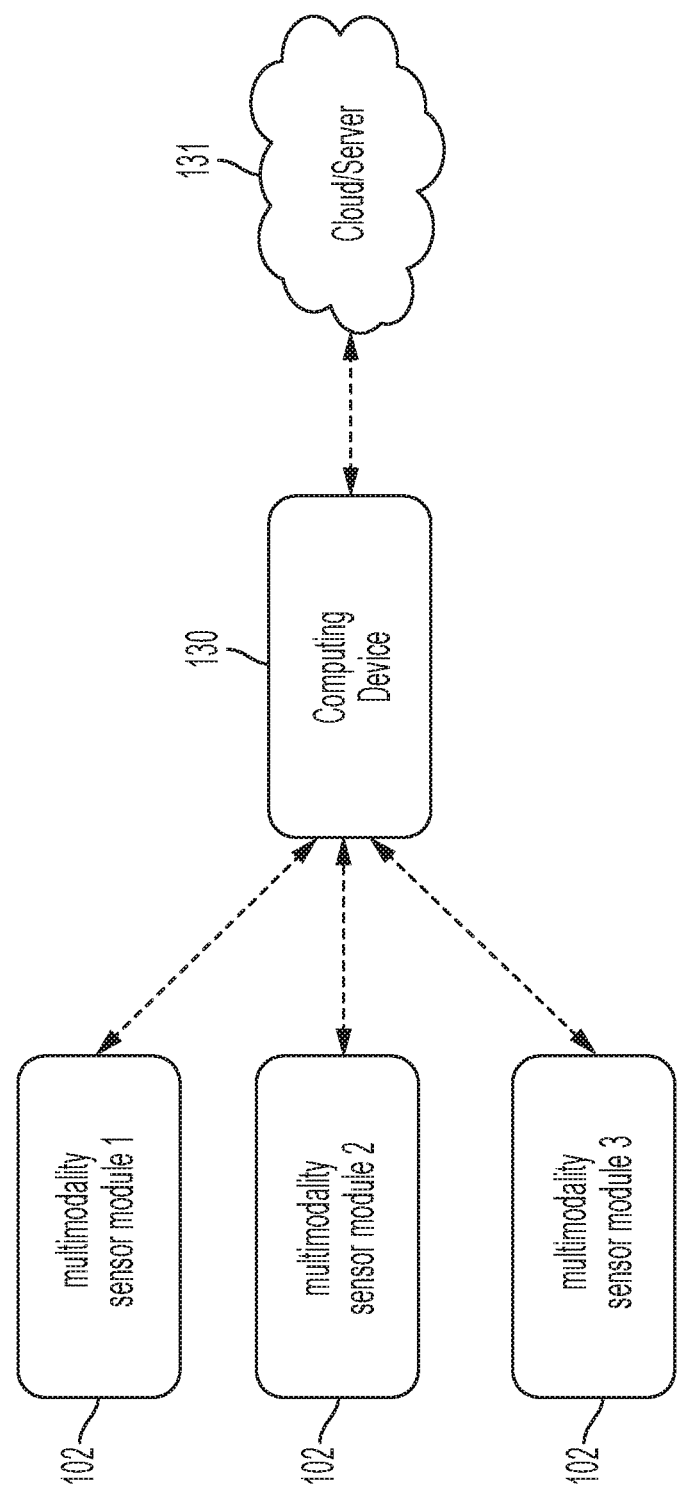
FIG. 6 is a schematic view of the system shown in FIG. 1.

PCB 112 generally includes a processor 124, memory 126 and communication module 128. By way of example only, communication module 128 may be configured for wireless communication (e.g., Bluetooth, LWAN (e.g., WiFi), or other similar connection) or wired connections (e.g., universal serial bus (USB) drive). With reference to FIG. 6, each universal multimodality sensor module 102 may communicate with each other universal multimodality sensor module 102 and/or a computing device 130, such as without limitation thereto, a mobile computing device (e.g., a smartphone, smartwatch or tablet computer) or a desktop computer (e.g., a personal computer (PC)). Computing device 130 may, in turn, communicate with a server over a network or cloud-based database 131.

Figure 1:
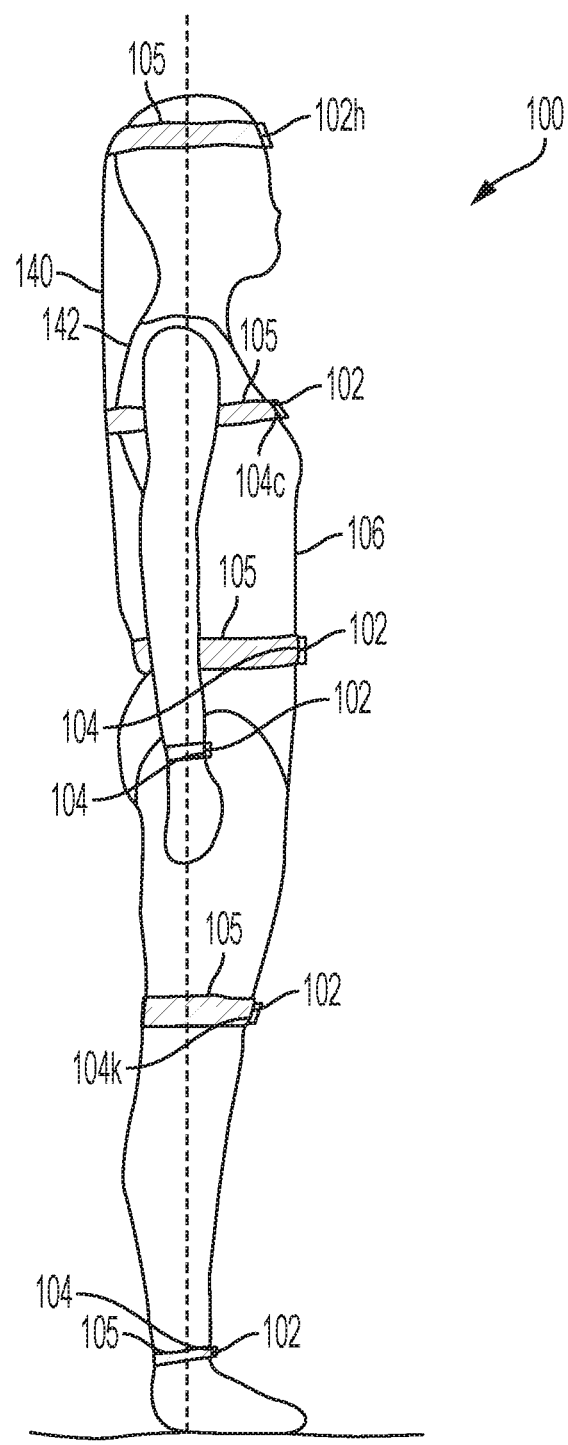
FIG. 1 is a side view of a system for monitoring and treating abnormal head, spine and body movements in accordance with an aspect of the present invention.
Figure 2:
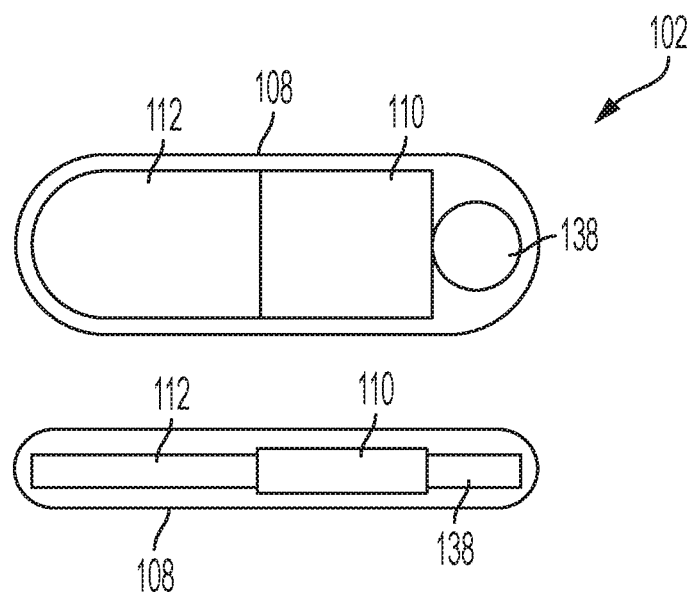
FIG. 2 are views of a universal multimodality sensor module suitable for use within the system shown in FIG. 1.
Figure 3:
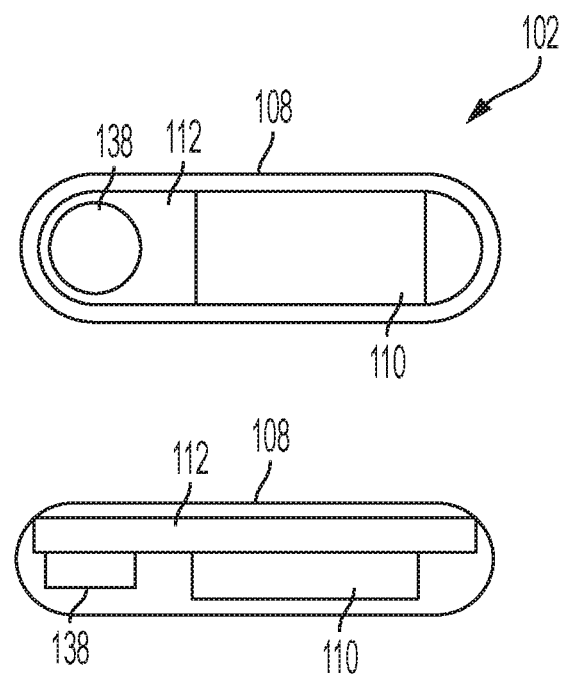
FIG. 3 are views of an alternative universal multimodality sensor module suitable for use within the system shown in FIG. 1.
Figure 4:
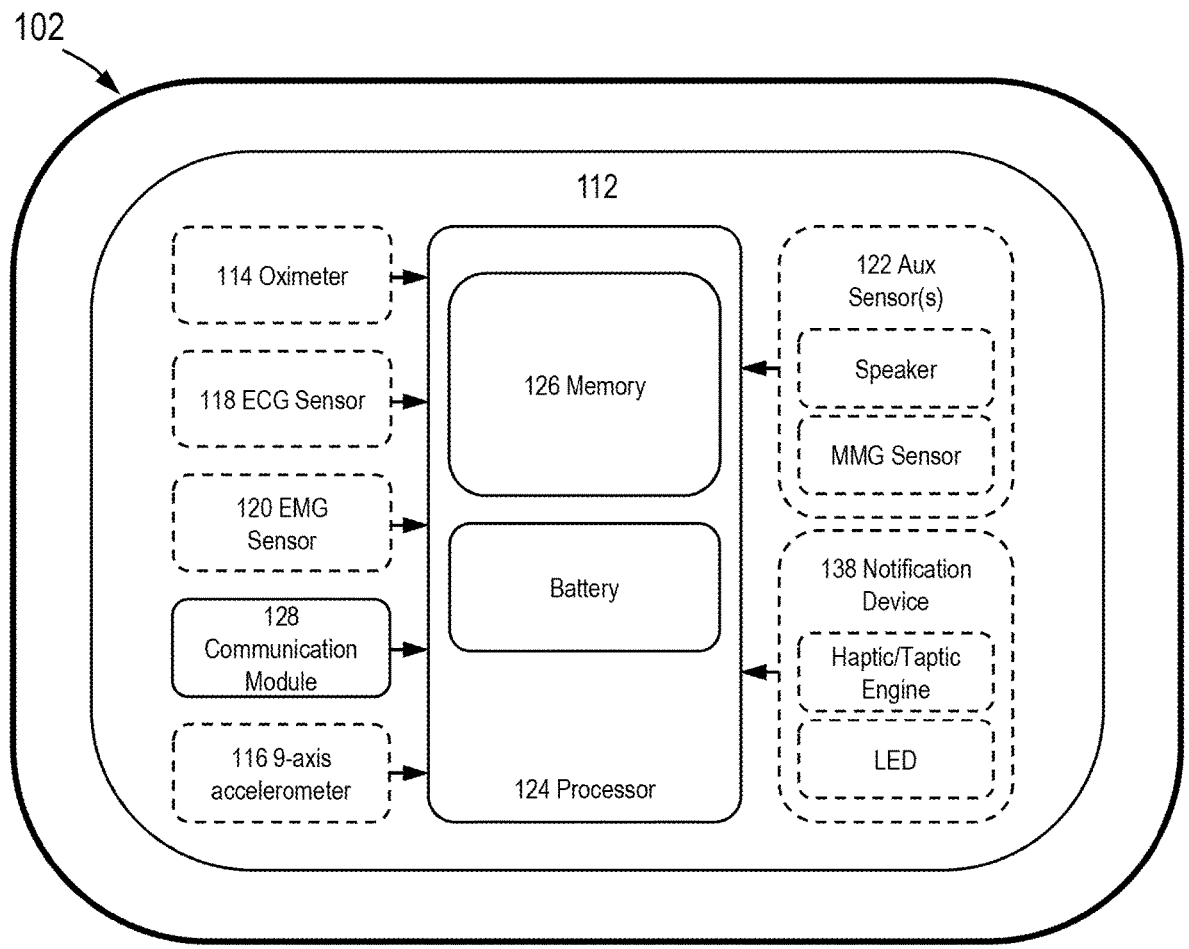
FIG. 4 is a plan view of a circuit board and associated sensors using within a universal multimodality sensor module shown in FIGS. 2 and 3.
Figure 5:
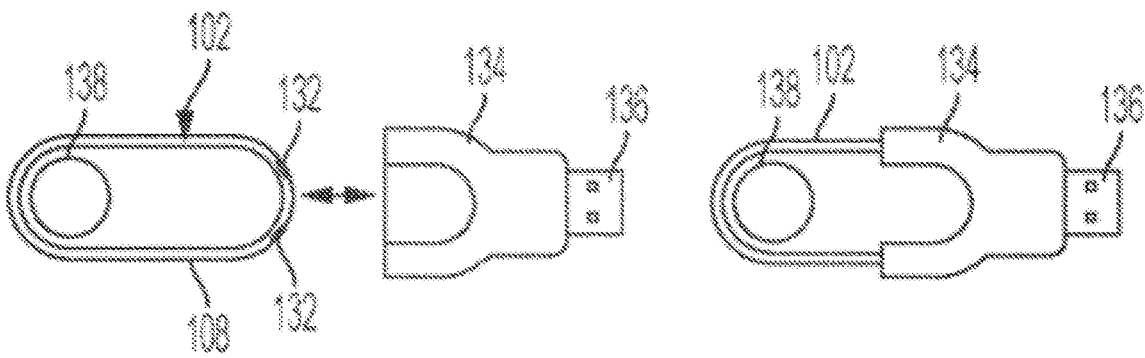
FIG. 5 is a top plan view of an embodiment of a universal multimodality sensor module received with a USB adapter.

As shown in FIG. 5, in accordance with another aspect of the present invention, battery 110 and/or communication module 128 may be coupled to one or more leads 132 on housing 108. Universal multimodality sensor module 102 may be slidingly received within a USB adapter 134 whereby leads 132 mate with corresponding contacts on USB plug 136 so that universal multimodality sensor module 102 may be coupled to computing device 130 to transfer information between universal multimodality sensor module 102 and computing device 130 and to charge rechargeable battery 110. Leads 132 may be sealed to housing 108 such that housing 108 is substantially watertight. In this manner, system 100 may be worn in the bath or shower without water entering and damaging the internal components of universal multimodality sensor modules 102.

As shown in FIG. 11, in accordance with a further aspect of the present invention, selected individual sensors within each respective multimodality sensor module are powered depending upon the selected location of its respective receiver unit on the wearer's body. In one aspect, leads 132 may also engage contacts within receiver units 104. In accordance with an aspect of the present invention, the contacts within receiver units 104 may be selectively differentiated so that receiver units with specific contacts may be located at specified locations on wearer 106. When universal multimodality sensor module 102 is coupled to a receiver unit 104, leads 132 may interpret the specific contacts whereby processor 124 may selectively control which sensors 114-122 are powered by battery 110 to receive health data from the wearer. In an additional or alternative aspect, computing device 130 may include a software application configured to selectively communicate with each individual universal multimodality sensor module 102. Wearer 106 (or a physician) may utilize the application to instruct each universal multimodality sensor module 102 which sensors 114-122 are to be powered and unpowered. By way of example, receiver unit 104c located at the chest of wearer 106 may power ECG sensor 118 while leaving oximeter 114 unpowered. Conversely, receiver unit 104k located proximate the knee of wearer 106 may power speaker/microphone 122 while leaving unpowered ECG sensor 118.

In accordance with another aspect of the present invention, 9-axis accelerometer 116 may be used to detect acceleration data resulting from a user tapping or double tapping any individual universal multimodality sensor module 102. In this manner, a wearer can double tap a universal multimodality sensor module 102 when pain is sensed, such as in the back, neck or other part of the body, during motion. Further detail of the related event or activity can be optionally recorded automatically via algorithms or manually in computing device 130, such as for example pain level, neurological deficit associated activities, etc. For example, a wearer can choose to record down pain lever during that moment in a scale from 1 to 10 while sensor data is uploaded to cloud-based database 131. This sensor data may include head and cervical-thoracic-lumbar spine data, as well as joint and other musculoskeletal or neurological status or cardiopulmonary parameters. In a further aspect of the invention, artificial intelligence may analyze the data from universal multimodality sensor modules 102 and provide accurate feedback that can be used by a health professional to monitor remote individual health status and notify a wearer to prevent and correct mal-position or injury or disease status.

In this manner, sensors 114-122 are capable of selectively detecting position, motion, neurological signal, blood oxygen level, ECG, EMG, MMG et al. By way of example, speaker/microphone 122 may detect joint friction auditory information will is collected and analyzed by processor 124 to determine whether there is pathological process (abrasion) between the articular cartilages. To continue this example, processor 124 may filter out noise with the filtered audio being then amplified. The amplified audio data may then be sent to computing device 130 and/or cloud-based database 131. The processor unit within computing device 130 (or another computer connected to cloud-based database 131) may analyze the audio data and, if potential pathological frequency is detected, notification may be sent to the wearer and/or a medical professional. It should be noted that system 100 may not only used in interrogating the skeletomuscular system, but may also be used with, for instance, the cardiovascular system to detected heart sounds, abnormal heart murmur, vascular bruits, the pulmonary system to detect breathing sounds and abnormal breathing sounds, and the gastrointestinal systems to detect bowel movement sounds. In a further example, system 100 may be used in conjunction with pregnant women to detect and monitor fetal movement and heartbeat.

Figure 10:
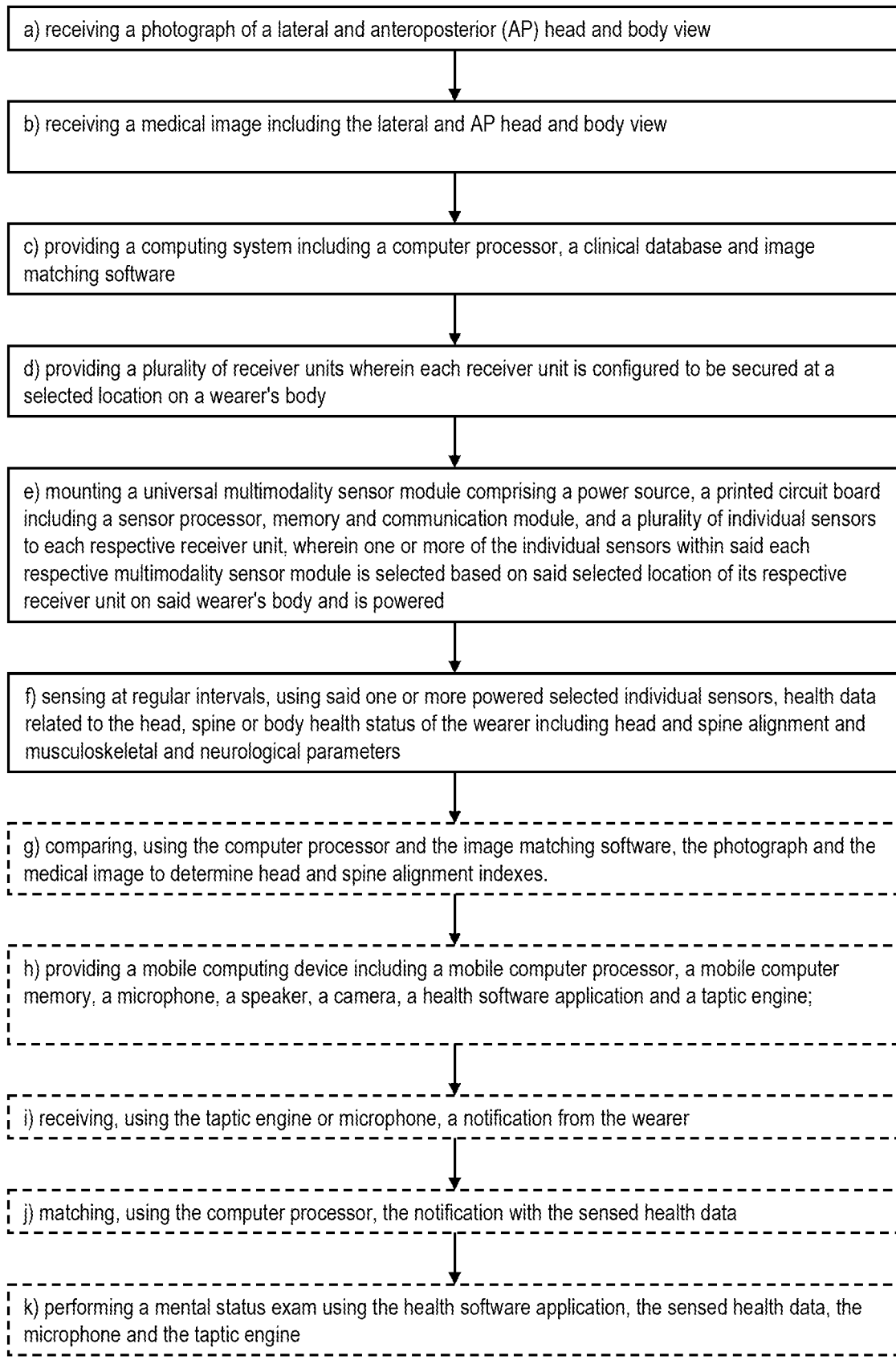
FIG. 10 shows a flowchart of a method according to an embodiment.

In a further aspect of the present invention, system 100 may include a notification device 138, such as a haptic/taptic engine and/or light emitting diode (LED). The output (e.g., sound, vibration or light) of notification device 138 may vary depending upon the location of the universal multimodality sensor module 102 chosen to issue the notification. The universal multimodality sensor module 102 chosen may be relevant to the need for notification. By way of example, if a notification regarding neck angle is needed, a universal multimodality sensor module 102 located at or near an ear may be chosen to issue an audio alarm through the speaker/microphone. Should the universal multimodality sensor module 102 be located on a band along the body, a vibration may be issued through the haptic/taptic engine (see FIG. 10). If universal multimodality sensor module 102 is located proximate hinge of 117 of eyeglasses/sunglasses 113 (See FIG. 7B) a tangent, LED light notification is used and will flash as a beam of light to lens 119. In a further aspect, notification of computing device 130 can also be activated to either vibrate or issue a sound alarm.

In accordance with an aspect of the present invention, a wearer may manually choose the notification method, such as through the software application on computing device 130. Different forms of notification may be considered due to convenience and accessibility, as well as battery usage. There may also be an emergency mode in order to protect the wearer. In the case of an injury or disorder, including traumatic brain injury, such as head shaking movements or neck pressure of the wearer close to the extremum, sudden trembling of the entire body, unreasonable bending beyond the normal range, fall without help or other emergency scenario detected by universal multimodality sensor modules 102, including but not limited to stroke, heart attack, seizure or loss of consciousness, notification device 138 will issue a sound (buzzer) alarm, vibration alarm, and an application notice. The alarm may also be sent to the pre-selected contacts such as a family member or medical professional/healthcare provider if an emergency were detected with no return to the normal range after a certain period depending upon the condition detected, such as traumatic brain injury, seizure, stroke, heart attack and/or spine cord injury. Emergency medication or instructions may also be provided via the software application before medical treatment arrives.

From the above discussion, it should be understood that system 100 may be used across a number of scenarios. For example, during sports or exercise, system 100 can detect and track dynamic head, spine and body part movement and stress and serve to correct the way a wearer moves that may result in injury and/or chronic disease. For the medical field, abnormal head, spine and body movement data can be collected and used to monitor and follow-up with patients with various disorders such a stroke, ADHD, Parkinson's disease, essential tremor, epilepsy, and spine and brain surgery patients.

Returning now to FIG. 1, in accordance with another aspect of the present invention, an active correction brace (ACB) 140 may be positioned along the head, neck and back 142 of wearer 106. ACB 140 includes an electronically adjustable elastic bandage that can selectively adjust the tightness degree of the bandage. Thus, should minor to moderate mal-position of the dynamic cervical and thoracic lumbar alignment be detected, the tension of ACB 140 may be adjusted so as to correct the wearer's body posture, including the positions of head, cervical-lumber vertebrae and pelvis, etc. As a result, head and spine biomechanical related injury and disease progression may be slowed or prevented. In the case of an injury or emergency, ACB 140 may be adjusted to output a correcting tension so as to intervene and prevent the excessive movement until medical personnel can arrive.

During the initial setup, cervical universal multimodality sensor modules 102h is worn around head area and compares the related positing to alignment from C2 to C7. 9-axis accelerometer 116 then uses both points as reference and is calibrated by flexing, extending and rotating the head and neck from neutral position for cervical calibration. Lumbar calibration can be initialized by standing or sitting against wall. All data is securely stored in memory 126, and no communication to computing device 130 or cloud-based database 131 is needed to access this calibrated data. Once calibration is completed, system 100 is ready for use, such as for a predetermined length of time (e.g., 1 week) before system 100 should be recalibrated. Optionally, during calibration, notification device 138 may be disabled to enable detection of a baseline. The notification device 138 may then be turned on for notification intervention as described above.

Figure 8:
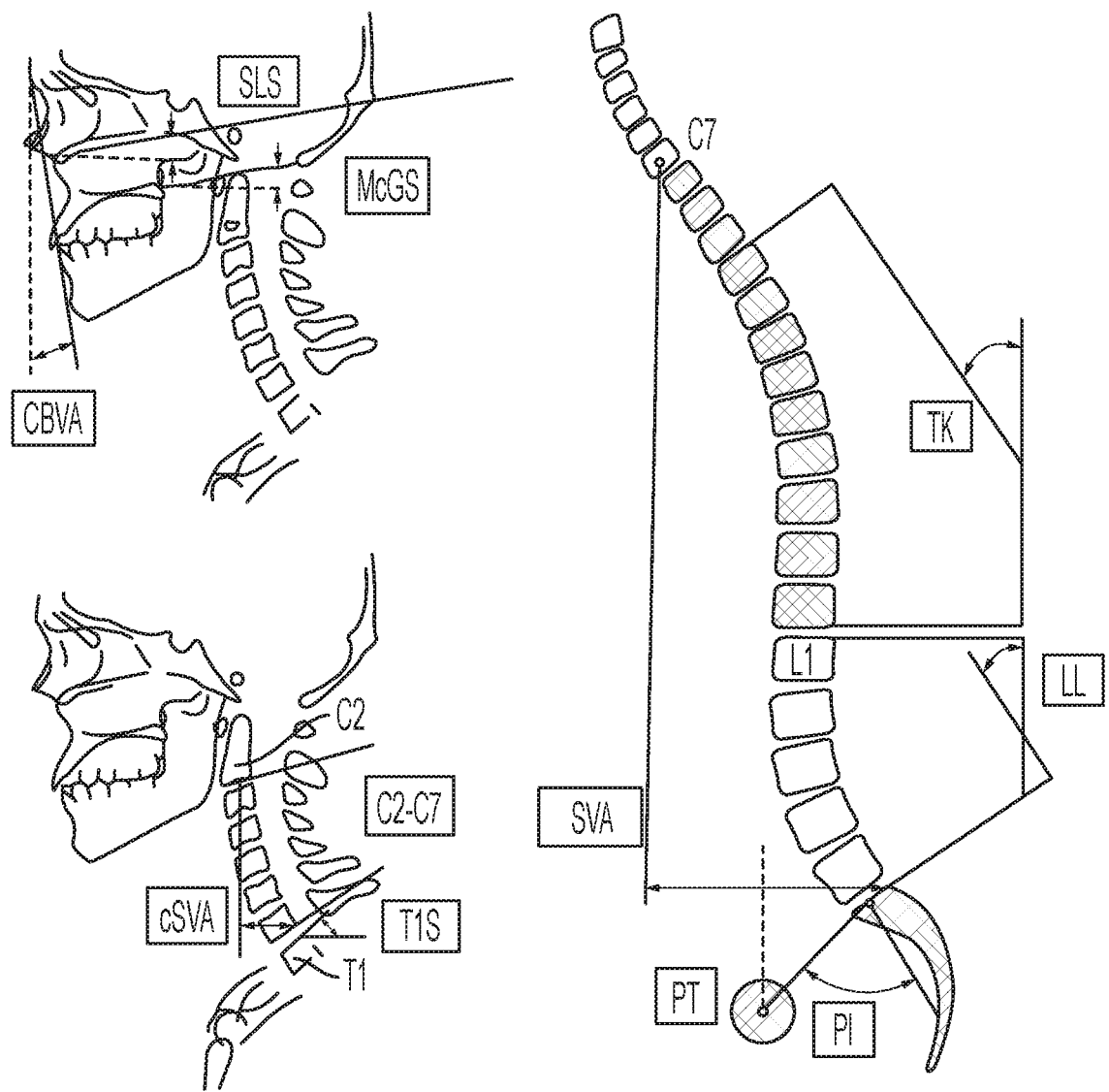
FIG. 8 shows global and regional alignment parameters for head and cervical spine, and thoracic lumbar spine.
Figure 9:
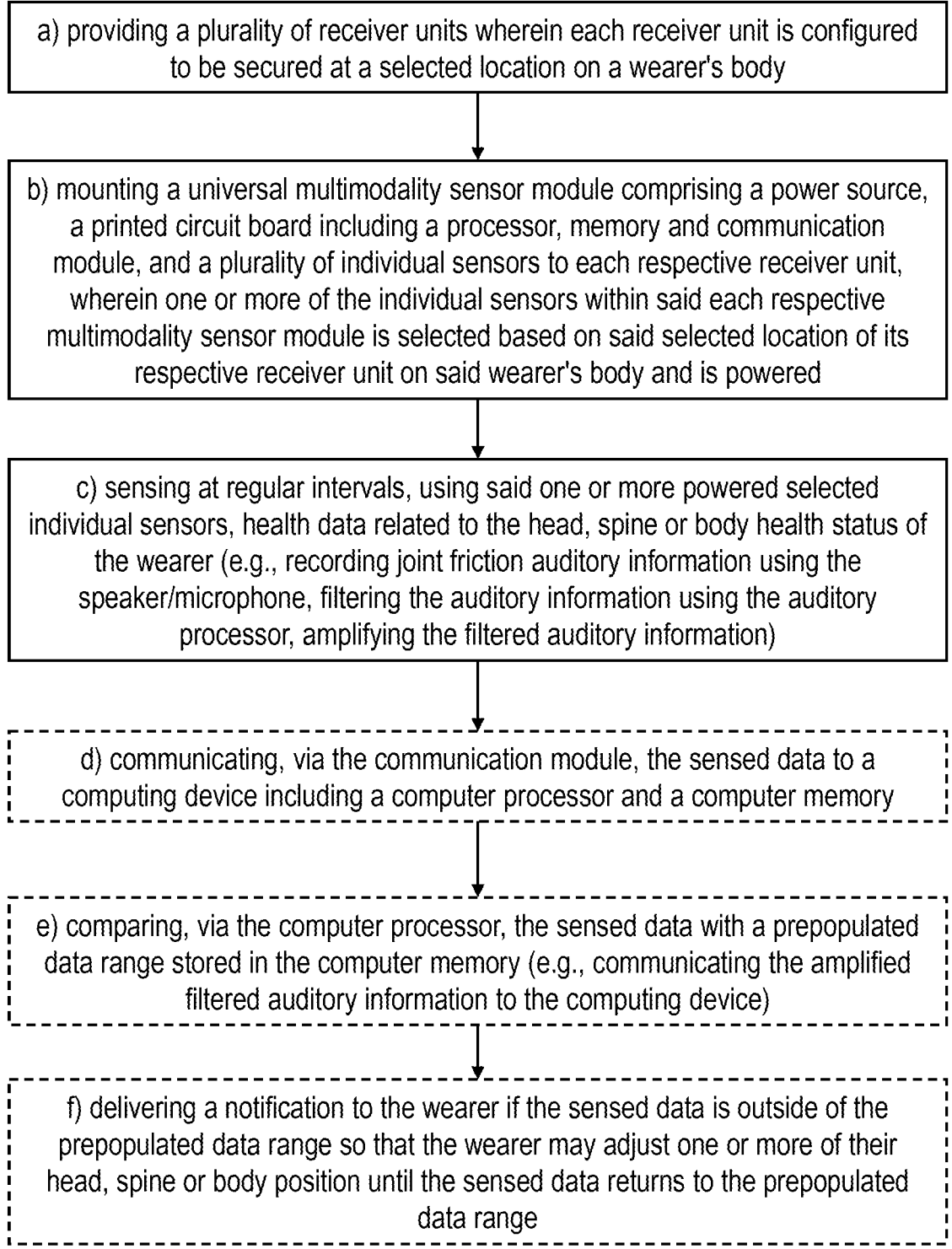
FIG. 9 shows a flowchart of a method according to an embodiment.

In accordance with a further aspect of the present invention, photographs of the lateral and anteroposterior (AP) head and body view can be taken by any suitable device, such as a cell phone or digital camera. These images can then be matched and compared with a medical image, such as X-ray, CT or MRI taken by a medical professional. By matching, comparing and combining the photograph and critical internal points with the medical images, analysis of head, spine and body photos provide detailed real-time head and spine alignment parameters, including cervical lordosis angle, chin-brow angle, cervical sagittal vertical axis (SVA), pelvic incidence, lumbar lordosis angle, pelvic tile, SVA, etc. (see FIG. 8). The critical spine alignment indexes may then be matched, calibrated and summarized through machine-learning. Thus, all the key cervical, thoracic and lumbar alignment indexes are measured through lateral and AP head and body photos without a complete battery of professional medical images, which are expensive and carry the risk of repeated exposure to radiation.

From the above and in accordance with an aspect of the present invention, a wearer's neurological status may be evaluated by system 100 through a minimal mental status exam including testing of 12 cranial nerve functions, a motor and sensation test, and coordination and gait assessment. Universal multimodality sensor modules 102 and the software application on computing device 130 can evaluate each component of the entire neurological system. Baseline and updated photographs, along with voice and sensor data, combined with the left and right asymmetric pattern enable a determination as to whether the wearer has any neurological deficits.

By way of example, the minimal mental status exam including orientation questions to time, place and person, short term and long term memory can evaluated by preset question options in the software application. Language evaluation can be performed by comprising real-time voice recordings with the pre-reordered baseline standard voice, and assisted by nonverbal hint in the application to determinate dysphagia or other oral impairment. The psychiatric evaluation can be performed through the software application using standard test batteries. The 12 cranial nerve tests include visual acuity and visual field. Pupil reaction can be evaluated by comparing baseline bilateral pupil size and reactive pupil size, shape and reactive pattern under flashlights emitted from computing device 130. Ocular movement innervated by the cranial nerve (CN) 3, 4, 6 can be recognized by bilateral eye neutral position and then movement pattern to all peripheral lateral directions by computing device 130. Facial sensation by CN5 is tested by touch feeling and reaction to the bilateral three facial zones to light touch. Facial pattern can be recognized by comparing baseline facial photos with and without smile with real-time facial photos taken by computing device 130 to see left and right asymmetric pattern difference. The bilateral hearing is evaluated by reaction to the sounds of different tone with different frequency and intensity. The open mouth view are taken to see the baseline and updated real-time photos after pronouncing particular sounds to see the left and right symmetric pattern change. Frontal view head and body photos may be taken to evaluate left and right shoulder height difference with and without the shoulder shrugging. The motor strength and motion pattern of bilateral body, upper and lower extremities can be performed by bilateral universal multimodality sensor modules 102 positioned around the left and right body, upper extremities like wrists and lower extremities like ankles. Movement pattern and speed difference may be compared, in addition to pressure data detected by the pressure sensor in computing device 130 after applying pressure on a designated screen area. The sensation is evaluated by a response to the preset vibration of the universal multimodality sensor module 102 or computing device 130 in different parts of the body and limb areas. The coordination function is detected by motion pattern and speed from the universal multimodality sensor module 102 to response to the upper and lower extremities coordination tests like hand-to-nose test or by detecting the accuracy of touching a still and moving object on the screen of computing device 130. Gait is evaluated by universal multimodality sensor modules 102 which acquire data including, but not limited to the gait speed, pattern, turning, initial, stop and rest break. The neurological exam, along with symmetry monitoring may be used to detect stroke, attention deficit/hyperactivity disorder (ADHD), Parkinson's disease, essential tremor, epilepsy and/or to monitor spine and brain surgery patients.

The foregoing description of the preferred embodiment of the invention has been presented for the purpose of illustration and description. It is not intended to be exhaustive nor is it intended to limit the invention to the precise form disclosed. It will be apparent to those skilled in the art that the disclosed embodiments may be modified in light of the above teachings. The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the following claims.

What is claimed is:

1. A method for monitoring and treating head, spine and body health comprising:
providing a plurality of receiver units wherein each receiver unit is configured to be secured at a selected location on a wearer's body;
mounting a universal multimodality sensor module comprising a power source, a printed circuit board including a processor, memory and communication module, and a plurality of individual sensors to each respective receiver unit, wherein one or more of the individual sensors within said each respective multimodality sensor module is selected based on said selected location of its respective receiver unit on said wearer's body and the selected one or more of the individual sensors is powered; and
sensing at regular intervals, using said one or more powered selected individual sensors, health data related to the head, spine or body health status of the wearer;
wherein the plurality of receiver units have contacts with configurations specific to the selected locations, the configurations causing selection of the one or more individual sensors;
when the universal multimodality sensor module is coupled to the receiver unit, leads interpret the specific contacts whereby one or more of the individual sensors are selected by the processor to power to receive the health data from the wearer.

2. The method of claim 1 further comprising:
communicating, via the communication module, the sensed data to a computing device including a computer processor and a computer memory,
comparing, via the computer processor, the sensed data with a prepopulated data range stored in the computer memory.

3. The method of claim 2 further comprising:
delivering a notification to the wearer if the sensed data is outside of the prepopulated data range so that the wearer may adjust one or more of their head, spine or body position until the sensed data returns to the prepopulated data range.

4. The method of claim 2 wherein each universal multimodality sensor module comprises a 9-axis accelerometer, a pulse oximeter, an electromyography (EMG) sensor and a mechanomyography (MMG) sensor.

5. The method of claim 4 wherein one or more of the universal multimodality sensor modules further comprises a feedback device in communication with the computing device, wherein when the sensed data is outside of the prepopulated data range the feedback device is triggered to deliver the notification.

6. The method of claim 5 wherein the feedback device comprises one or both of a haptic device configured to vibrate and a light emitting diode (LED) configured to emit a steady light or flashing light.

7. The method of claim 4 wherein one or more of the universal multimodality sensor modules further comprises a speaker/microphone and auditory processor, wherein the method further includes:
   recording joint friction auditory information using the speaker/microphone;
   filtering the auditory information using the auditory processor;
   amplifying the filtered auditory information; and
   communicating the amplified filtered auditory information to the computing device.

8. The method of claim 7 wherein the speaker/microphone is a bone conduction speaker/microphone.

9. The method of claim 2 wherein a first universal multimodality sensor module senses health data from a wearer's left arm and wherein a second universal multimodality sensor module senses health data from a wearer's right arm, and wherein the computer processor compares the left arm health data to the right arm health data to identify symmetry between the left arm and the right arm.

10. The method of claim 2 wherein the computing device is a mobile computing device.

11. The method of claim 4 wherein one or more of the universal multimodality sensor modules further comprises a selectively switchable speaker/microphone, wherein the speaker/microphone can be selectively activated to record patient generated data in combination with the sensed health data.

12. A system for monitoring and treating head, spine and body health status comprising:
   a plurality of receiver units wherein each receiver unit is configured to be secured at a selected location on a wearer's body; and
   a plurality of universal multimodality sensor modules, each comprising one or more individual sensors, a power source, a printed circuit board including a processor, memory and communication module, wherein a respective multimodality sensor module is coupled with a respective receiver,
   wherein one or more of the individual sensors within said each respective multimodality sensor module is selected based on said selected location of its respective receiver unit on said wearer's body and the selected one or more of the individual sensors is powered,
   wherein health data related to the head, spine or body movements of the wearer is sensed at regular intervals using said one or more powered selected individual sensors, and
   wherein the plurality of receiver units have contacts with configurations specific to the selected locations, the configurations causing selection of the one or more individual sensors;
   when the universal multimodality sensor module is coupled to the receiver unit, leads interpret the specific contacts whereby one or more of the individual sensors are selected by the processor to power to receive the health data from the wearer.

13. The system of claim 12 further comprising:
   a computing device including a computer processor and a computer memory, wherein the communication module communicates the sensed data to the computer processor whereby the computer processor compares the sensed data with a prepopulated data range stored in the computer memory.

14. The system of claim 13 wherein each universal multimodality sensor module comprises a 9-axis accelerometer, a pulse oximeter, an electromyography (EMG) sensor and a mechanomyography (MMG) sensor.

15. The system of claim 14 wherein one or more of the universal multimodality sensor modules further comprises a feedback device in communication with the computing device, wherein when the sensed data is outside of the prepopulated data range the feedback device is triggered to deliver the notification.

16. The system of claim 15 wherein the feedback device comprises one or both of a haptic device configured to vibrate and a light emitting diode (LED) configured to emit a steady light or flashing light.

17. The system of claim 14 wherein one or more of the universal multimodality sensor modules further comprises a speaker/microphone and auditory processor, wherein joint friction auditory information is recorded by the speaker/microphone, filtered and amplified by the auditory processor and communicated to the computing device.

18. The system of claim 17 wherein the speaker/microphone is a bone conduction speaker/microphone.

19. The system of claim 12 wherein a first universal multimodality sensor module senses health data from a wearer's left arm and wherein a second universal multimodality sensor module senses health data from a wearer's right arm, and wherein the computer processor compares the left arm health data to the right arm health data to analyze symmetry between the left arm and the right arm.

20. The system of claim 14 wherein one or more of the universal multimodality sensor modules further comprises a selectively switchable speaker/microphone, wherein the speaker/microphone can be selectively activated to record patient generated data in combination with the sensed health data.

21. A method for monitoring and treating head, spine and body health comprising:
   receiving a photograph of a lateral and anteroposterior (AP) head and body view;
   receiving a medical image including the lateral and AP head and body view;
   providing a computing system including a computer processor, a clinical database and image matching software;
   providing a plurality of receiver units wherein each receiver unit is configured to be secured at a selected location on a wearer's body;
   mounting a universal multimodality sensor module comprising a power source, a printed circuit board including a sensor processor, memory and communication module, and a plurality of individual sensors to each respective receiver unit, wherein one or more of the individual sensors within said each respective multimodality sensor module is selected based on said selected location of its respective receiver unit on said wearer's body and the selected one or more of the individual sensors is powered;
   sensing at regular intervals, using said one or more powered selected individual sensors, health data related to the head, spine or body health status of the wearer including head and spine alignment and musculoskeletal and neurological parameters; and comparing, using the computer processor and the image matching software, the photograph and the medical image to determine head and spine alignment indexes;

wherein the plurality of receiver units have contacts with configurations specific to the selected locations, the configurations causing selection of the one or more individual sensors;

when the universal multimodality sensor module is coupled to the receiver unit, leads interpret the specific contacts whereby one or more of the individual sensors are selected by the processor to power to receive the health data from the wearer.

22. The method of claim 21 wherein the sensed health data includes a measurement of spine dynamic angle, wherein determination of the head and spine alignment indexes includes comparing the spine dynamic angle with the photograph and the medical image.

23. The method of claim 21, further comprising the steps of:
providing a mobile computing device including a mobile computer processor, a mobile computer memory, a microphone, a speaker, a camera, a health software application and a taptic engine;
receiving, using the taptic engine or microphone, a notification from the wearer; and
matching, using the computer processor, the notification with the sensed health data.

24. The method of claim 23 further comprising the step of:
performing a mental status exam using the health software application, the sensed health data, the microphone and the taptic engine.

25. The method of claim 24 wherein the health software application presents and records a wearer responses to orientation questions, performs a psychiatric evaluation using standard test batteries, and wherein the camera detects pupil reaction, bilateral eye neutral position, a movement pattern of the wearer's eyes, facial sensation, facial symmetry and mouth symmetry, and wherein the camera and speaker perform a bilateral hearing test by evaluating the wearer's reaction to sounds of different tones, frequencies and intensities, and wherein the microphone determines dysphagia or other oral impairment, and wherein the taptic engine detects motor strength, motor movement and speed, and wherein a first universal multimodality sensor module is positioned on a left limb of the wearer and a second universal multimodality sensor module is positioned on a right limb of the wearer whereby the first and second universal multimodality sensor modules record wearer coordination and symmetry of the wearer's limbs.

26. The method of claim 23 further comprising the step of:
recording the notification automatically by the computer processor or manually by the wearer double tapping the taptic engine of the mobile computing device.

27. The method of claim 26 further comprising the step of:
inputting additional detail on the mobile computing device using one or more of the taptic engine, the microphone and the camera.

28. The method of claim 27 further comprising the step of:
communicating the additional detail to the computing system.

29. The method of claim 21 wherein one or more of the universal multimodality sensor modules further comprises a speaker/microphone and auditory processor, wherein joint friction auditory information is recorded by the speaker/microphone, filtered and amplified by the auditory processor and matched to data within the clinical database of the computing system.

30. The method of claim 21 wherein the step of determining head and spine alignment indexes includes cervical and lumbar spine calibration.

31. The method of claim 30 wherein the cervical and lumbar spine calibration can be initialized by standing or sitting against wall.

32. The method of claim 21 further comprising the steps of:
coupling an active correction brace (ACB) comprising an electronically adjustable elastic bandage to two or more receiver units or universal multimodality sensor modules; and
automatically adjusting the tension on the ACB when the sensed data is outside of a prepopulated data range.

33. The method of claim 21 further comprising the step of:
providing a cloud-based health database in communication with the communication module each of the universal multimodality sensor modules and the computing device.

34. The method of claim 33 wherein the cloud-based health database employs machine learning to monitor the sensed health data and adjust the optimal head and spine alignment indexes.

* * * * *